(12) United States Patent
Pinkos et al.

(10) Patent No.: US 8,183,411 B2
(45) Date of Patent: May 22, 2012

(54) PROCESS FOR PREPARING 6-HYDROXYCAPROIC ESTERS

(75) Inventors: Rolf Pinkos, Bad Duerkheim (DE); Tilman Sirch, Schifferstadt (DE); Gerd-Dieter Tebben, Mannheim (DE); Rolf-Hartmuth Fischer, Heidelberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/867,509

(22) PCT Filed: Jan. 29, 2009

(86) PCT No.: PCT/EP2009/051000
§ 371 (c)(1), (2), (4) Date: Aug. 13, 2010

(87) PCT Pub. No.: WO2009/100989
PCT Pub. Date: Aug. 20, 2009

(65) Prior Publication Data
US 2011/0015429 A1    Jan. 20, 2011

(30) Foreign Application Priority Data

Feb. 15, 2008 (EP) ..................... 08101692

(51) Int. Cl.
*C07C 51/42* (2006.01)
(52) U.S. Cl. ...................................... 562/580
(58) Field of Classification Search ............... None
See application file for complete search history.

(56) References Cited

U.S. PATENT DOCUMENTS

| | | | | |
|---|---|---|---|---|
| 3,277,168 | A * | 10/1966 | Koenig ............ | 562/580 |
| 3,772,375 | A * | 11/1973 | Brunie et al. ........ | 562/579 |
| 3,848,003 | A * | 11/1974 | Mesich et al. ....... | 568/864 |
| 3,855,319 | A * | 12/1974 | Hobbs et al. ........ | 568/864 |
| 6,015,924 | A | 1/2000 | Le Bris | |
| 6,063,958 | A | 5/2000 | Chen et al. | |
| 2011/0124926 | A1 * | 5/2011 | Pinkos et al. ....... | 568/864 |

FOREIGN PATENT DOCUMENTS

| | | |
|---|---|---|
| DE | 19 51 250 | 4/1970 |
| DE | 2 358 460 | 5/1974 |
| DE | 197 38 464 | 3/1999 |
| EP | 0 847 979 | 6/1998 |
| FR | 1 505 363 | 12/1967 |

OTHER PUBLICATIONS

U.S. Appl. No. 13/133,006, filed Jun. 6, 2011, Abillard, et al.
U.S. Appl. No. 13/257,496, filed Sep. 19, 2011, Pinkos, et al.
U.S. Appl. No. 13/258,166, filed Sep. 21, 2011, Pinkos, et al.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The present application relates to an improved process for preparing 6-hydroxycaproic esters from the by-product mixtures which are obtained in the oxidation of cyclohexane to cyclohexanol and cyclohexanone with oxygen or oxygen-comprising gas mixtures.

26 Claims, 1 Drawing Sheet

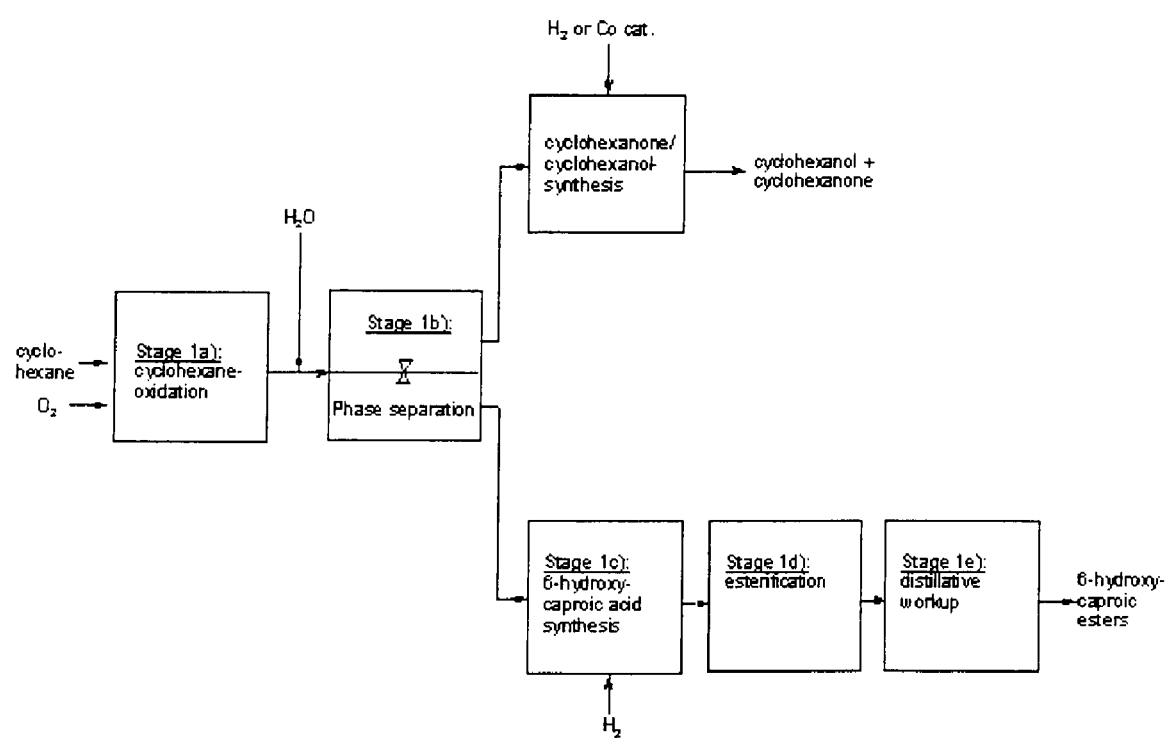

PROCESS FOR PREPARING 6-HYDROXYCAPROIC ESTERS

CROSS REFERENCE TO RELATED APPLICATION

This application is a 371 of PCT/EP09/051000, filed on Jan. 29, 2009, and claims priority to European Patent Application No. 08101692.5, filed on Feb. 15, 2008.

The present application relates to an improved process for preparing 6-hydroxycaproic esters from the by-product mixtures which are obtained in the oxidation of cyclohexane to cyclohexanol and cyclohexanone with oxygen or oxygen-comprising gas mixtures.

6-Hydroxycaproic acid and the esters of 6-hydroxycaproic acid can be cyclized to ε-caprolactone. ε-Caprolactone and the polycaprolactones formed therefrom by polyaddition serve for preparation of polyurethanes.

It is known that the oxidation of cyclohexane to cyclohexanol and cyclohexanone can be carried out either in one stage in the presence of cobalt compounds as catalysts, or in two stages.

In the two-stage method, the first step works without catalyst. The cyclohexyl hydroperoxide formed is converted to cyclohexanol and cyclohexanone in the second step in the presence of a cobalt catalyst, as described by Arpentinier et al. in The technology of catalytic oxidations, Editions Technip 2001, page 227, paragraphs 1 and 3.

DE-A 2 358 460 also already discloses the hydrogenation of cyclohexyl hydroperoxide dissolved in aqueous or organic solvents to cyclohexanol in the presence of noble metal catalysts.

DE-A 1 951 250 and EP-B 847 979 teach how 6-hydroxycaproic acid can be obtained from the products of the two-stage cyclohexanol preparation. To this end, cyclohexane is oxidized in the liquid phase in the absence of a catalyst. The oxidation output, which comprises mainly cyclohexyl hydroperoxide, cyclohexanol, cyclohexanone and products of further oxidation, such as 6-hydroperoxycaproic acid, 6-hydroxycaproic acid, adipic acid, succinic acid, glutaric acid and also 5-formylvaleric acid, as described in example 1, line 19, and example 3, line 47, and in paragraph [0005] of EP-B 847 979 under the names "semialdehyde adipiquet" or "acide formyl-5-valerique", is admixed with water. The reaction mixture which is then biphasic is separated into an organic phase and an aqueous phase.

The organic phase is, as already described, converted to cyclohexanol and cyclohexanone by deperoxidation with metal compounds or by catalytic hydrogenation.

As well as 6-hydroperoxycaproic acid, the water phase comprises 6-hydroxycaproic acid, 5-formylvaleric acid, adipic acid, succinic acid and glutaric acid.

In order to convert 6-hydroperoxycaproic acid to 6-hydroxycaproic acid, the water phase, according to DE-A 1 951 250, is hydrogenated in the presence of palladium, rhodium or platinum catalysts at from 15 to 130° C., preferably from 50 to 100° C., and pressures of from 2 to 20 bar.

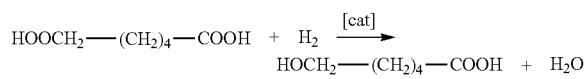

The metals mentioned may be applied to supports such as SiO2, Al2O3, activated carbon or aluminosilicate. The three examples work with a supported catalyst which comprises 10% by weight of palladium on activated carbon.

A disadvantage in the hydrogenation of 6-hydroperoxycaproic acid according to DE-A 1 951 250 is that the 5-formylvaleric acid present in the water phase is not hydrogenated fully to 6-hydroxycaproic acid at from 15 to 130° C. and from 2 to 20 bar in the presence of the noble metal catalysts mentioned. The esterification of 6-hydroxycaproic acid and subsequent distillative purification affords a mixture of 6-hydroxycaproic esters, 5-formylvaleric esters and acetals thereof, since all esters possess very similar vapor pressures. A full distillative removal of the formylvaleric esters would be possible only with a high level of distillation complexity, associated with high energy costs.

It was therefore an object of the invention to provide hydrogenation catalysts and hydrogenation conditions with which 6-hydroperoxycaproic acid and 5-formylvaleric acid can be hydrogenated with high yields to 6-hydroxycaproic acid.

This object is achieved by a process for preparing 6-hydroxycaproic esters, wherein
 a) cyclohexane is oxidized with molecular oxygen or mixtures of molecular oxygen and gases which are inert under the reaction conditions to give a reaction mixture which comprises, as main components, cyclohexyl hydroperoxide, cyclohexanol, cyclohexanone, unconverted cyclohexane, 6-hydroperoxycaproic acid, 6-hydroxycaproic acid, 5-formylvaleric acid and α,ω-dicarboxylic acids having from four to six carbon atoms,
 b) the reaction mixture from step a), after adding water, is separated into an organic phase comprising cyclohexane and the cyclohexane compounds, and an aqueous phase comprising the carboxylic acids,
 c) the aqueous phase from b) is catalytically hydrogenated,
 d) the carboxylic acids present in the aqueous phase are reacted with an alcohol comprising from 1 to 10 carbon atoms to give the corresponding carboxylic esters and
 e) 6-hydroxycaproic esters are obtained by distillation from the esterification mixture from step d),
the catalytic hydrogenation in step c) involving at least hydrogenation of 5-formylvaleric acid to 6-hydroxycaproic acid.

The process according to the invention is advantageous when step a) is performed in the presence of a catalyst.

The process according to the invention is advantageous when step a) is performed in the absence of a catalyst.

The process according to the invention is advantageous when not only 5-formylvaleric acid but also 6-hydroperoxycaproic acid is hydrogenated in step c) to 6-hydroxycaproic acid.

The process according to the invention is advantageous when the aqueous phase comprising the carboxylic acids from step b), to remove residual amounts of cyclohexyl hydroperoxide, cyclohexanol and cyclohexanone, is extracted with an aliphatic, cycloaliphatic or aromatic hydrocarbon.

The process according to the invention is advantageous when 6-hydroperoxycaproic acid and 6-hydroxycaproic acid are extracted from the aqueous phase of step b) with an organic, inert solvent from the water phase.

The process according to the invention is advantageous when the aqueous phase comprising the carboxylic acids from step b) is concentrated by distilling water off and the carboxylic acids which precipitate out in solid form are removed.

The process according to the invention is advantageous when the hydrogenation in step c) is performed in the presence of catalysts which comprise at least one metal of groups 7 to 12 of the Periodic Table, excluding Pt, Pd and Rh where they are the sole catalytic components.

The process according to the invention is advantageous when the catalyst metal used for the hydrogenation in step c) is at least one metal selected from ruthenium, nickel, cobalt, rhenium and copper.

The process according to the invention is advantageous when the hydrogenation in step c) is performed at temperatures of from 100 to 200° C. and pressures of from 1 to 100 bar.

In the process according to the invention, cyclohexanol and cyclohexanone can also be obtained from the organic phase of step b).

The two-stage preparation of cyclohexanol and cyclohexanone from cyclohexane is known. Arpentinier et al., The technology of catalytic oxidation, Edition Technip 2001, page 227, third paragraph, discloses that hydroperoxides are prepared in the first step. Operation is effected in the absence of catalysts. In the second step, the cyclohexyl hydroperoxide removed is decomposed in the presence of a cocatalyst to cyclohexanol and cyclohexanone. The process works with a cyclohexane conversion of from 4 to 5%, a cyclohexanol/cyclohexanone selectivity in the range from 82 to 86% and a cyclohexanol/cyclohexanone ratio of 0.4.

DE-A 1 951 250, page 2, second paragraph, discloses the performance of the catalyst-free oxidation of cyclohexane with short residence times and comparatively low temperatures in apparatus whose surface does not catalyze the decomposition of hydroperoxides.

FR-A 1 505 363 comprises, at page 4, left-hand side, second paragraph, a method for catalyst-free oxidation of cyclohexane. In this method, cyclohexane is oxidized with air whose oxygen content has been depleted to from 13 to 14 percent by volume. Operation is effected at from 170 to 180° C. and a pressure of 18 bar in an apparatus made of nonoxidizable steel which has been passivated with pyrophosphate. The oxidation is ended as soon as the oxidate comprises 4% by weight of products which have higher boiling points than cyclohexane.

It is also possible to use cyclohexane oxidates which have been obtained in the presence of from 0.1 to 300 ppm, preferably from 0.1 to 200 ppm, more preferably from 0.1 to 100 ppm, of a deperoxidation catalyst, based on cyclohexane. Suitable deperoxidation catalysts are cobalt compounds which are soluble in cyclohexane under the oxidation conditions. Examples thereof are cobalt salts of carboxylic acids, for example cobalt naphthenate, cobalt stearate or cobalt octoate. The content of hydroperoxides in the oxidation output increases with increasing content of oxidation catalyst.

Preference is given to catalyst-free cyclohexane oxidation over catalyzed cyclohexane oxidation.

In the process according to the invention, in step b), the oxidation output of the cyclohexane oxidation, as described in DE-A 1 951 250, is admixed with water. In the process according to the invention, outputs from uncatalyzed cyclohexane oxidation are used for this purpose. However, outputs from catalyzed cyclohexane oxidation are also possible.

The oxidation outputs can be concentrated by distilling cyclohexane off. The oxidation outputs comprise, if appropriate after distilling off some of the cyclohexane, at least 10% by weight, preferably at least 30% by weight, more preferably at least 50% by weight, of hydroperoxides, based on the oxidized products, which are heavier than cyclohexane.

The oxidation output of the cyclohexane oxidation is, according to DE-A 1 951 250, admixed in the liquid phase, if appropriate after distilling cyclohexane off, with from 0.01 to 10 times the amount by weight of water, based on the amount of oxidation output, at temperatures between 5 and 100° C., preferably between 15 and 30° C., under autogenous pressure or under pressure, by means of an inert gas when the temperature selected is above the boiling point of the azeotropic water/cyclohexane mixture.

The oxidation output divides into two liquid phases after addition of water: an organic phase which comprises cyclohexyl hydroperoxide, cyclohexanol, cyclohexanone and unconverted cyclohexane, and an aqueous phase which comprises 6-hydroperoxycaproic acid, 5-hydroxyvaleric acid, 6-hydroxycaproic acid, adipic acid, succinic acid, glutaric acid and 5-formylvaleric acid, monocarboxylic acids having from 1 to 6 carbon atoms, 1,2- and 1,4-cyclohexanediones, and a multitude of small amounts of further by-products.

The biphasic liquid reaction mixture is separated in step b) of the process according to the invention into a liquid organic phase and a liquid aqueous phase.

The reaction of the oxidation output with water and the subsequent phase separation can be carried out batchwise or continuously, preferably continuously.

The liquid organic phase removed in step b) can be worked up to prepare cyclohexanol and cyclohexanone. For this purpose, the liquid organic phase from step b) is converted by deperoxidation with metal compounds or by catalytic hydrogenation to mixtures of cyclohexanol and cyclohexanone.

In the deperoxidation of cyclohexyl hydroperoxide to cyclohexanol and cyclohexanone, the liquid organic phase is admixed with from 1 to 300 ppm of a metal compound. Preference is given here to cobalt salts of carboxylic acids, for example cobalt naphthenate or cobalt octoate. Operation is effected at from 120 to 200° C. and autogenous pressure of the system or pressures up to 5 bar, which are generated by inert gases.

The deperoxidation can be carried out batchwise, but preferably continuously.

The hydrogenation of cyclohexyl hydroperoxide to cyclohexanol/cyclohexanone mixtures can be effected according to DE-A 2 358 460 in the presence of finely distributed, suspended catalysts based on the noble metals of transition group 8 of the Periodic Table of the Elements: ruthenium, rhodium, palladium, osmium, iridium, platinum. Preference is given to the elements palladium, rhodium and platinum. The hydrogenation is carried out at temperatures of from 20 to 180° C., especially from 50 to 100° C. The partial hydrogen pressure is from 0.1 to 50 at, preferably 10 at, especially from 1 to 2 at. In 12 examples, the catalysts used were 10% Pd on activated carbon, 4.1% Pd+1.1% Pt on activated carbon, 5% Pd on $Al_2O_3$ and 1% Pd on $SiO_2$ in suspended form. Hydrogenation was effected at from 30 to 60° C. and partial hydrogen pressure 1 at in cyclohexane as a solvent.

According to FR-A 1 505 363, on page 2, right-hand column, last paragraph, catalysts based on palladium, rhodium, rhenium and nickel, preferably of palladium and rhodium, are used for the catalytic hydrogenation of cyclohexyl hydroperoxide in cyclohexane as a solvent. The metals are applied to acidic or neutral supports. Examples of such supports are, for example, activated carbon, $SiO_2$ or $Al_2O_3$. Hydrogenation is effected at from 80 to 100° C. and from 10 to 20 bar. Before the hydrogenation, water is added to the reaction mixture. Above 100° C., undesired side reactions increase.

The hydrogenation can be carried out in one reactor or in a plurality of reactors connected in series. In an embodiment preferred in FR-A 1 505 363, operation is effected in a column which comprises a fixed bed supported catalyst.

The hydrogenation can be performed batchwise, but preferably continuously.

The aqueous phase removed in step b) in the process according to the invention comprises, as main products, 6-hydroperoxycaproic acid, 6-hydroxycaproic acid, 5-hydroxyvaleric acid, 1,2- and 1,4-cyclohexanediones, 1,2- and 1,4-cyclohexanediols, carboxylic acids having from one to six carbon atoms, adipic acid, succinic acid, glutaric acid and 5-formylvaleric acid. This aqueous phase can be used directly for the catalytic hydrogenation to prepare 6-hydroxycaproic acid.

Residual amounts of cyclohexyl hydroperoxide, cyclohexanol and cyclohexanone which may not have been removed from the aqueous phase in the phase separation in step b) of the process according to the invention can, however, be removed by subsequent extraction if appropriate. The extractants used may be aliphatic, cycloaliphatic or aromatic hydrocarbons such as n-octane, dodecane, hexane, toluene, xylene, cyclohexane, methylcyclohexane, cyclooctane, cyclododecane or mixtures of these compounds. When cyclohexane is used as the extractant, the extract can be combined directly with the cyclohexane phase from step b) of the process according to the invention.

A further means of lowering the by-product content in the aqueous phase consists in concentrating the water phase. It is performed at temperatures below 50° C. and under reduced pressure in order not to bring about any thermal decomposition of the hydroperoxycaproic acid. In the concentration of the water phase, dicarboxylic acids, especially adipic acid, precipitate out of the aqueous phase. They can be removed by filtration or centrifugation. It is advantageous to remove a portion of the dicarboxylic acids and in particular adipic acid at this point in the process. Otherwise, in step d) of the process according to the invention, the entire amount of dicarboxylic acids is transesterified with low molecular weight alcohols to give dicarboxylic esters.

The subsequent distillative removal of the adipic diesters from corresponding 6-hydroxycaproic esters in step e) of the process according to the invention is, however, associated with high energy demands.

However, it is also possible to extract 6-hydroperoxycaproic acid and 6-hydroxycaproic acid from the aqueous phase with organic solvents and then to use the organic extracts for the catalytic hydrogenation. Solvents which are inert under the hydrogenation conditions include, according to U.S. Pat. No. 3,277,168 and DE-A 1 951 250, page 5, alkanols having from four to ten carbon atoms, cycloalkanols having from five to eight carbon atoms, esters of alkanecarboxylic acids having from two to eight carbon atoms, and alkanols having from one to eight carbon atoms.

It is also possible to deperoxidize the 6-hydroperoxycaproic acid, as in the case of cyclohexyl hydroperoxide, by adding cobalt compounds to 6-hydroxycaproic acid and then to hydrogenate the resulting reaction mixture.

It is likewise possible to extract 6-hydroxycaproic acid and 5-formylvaleric acid from the deperoxidized reaction mixture and to send the extract to a hydrogenation.

For the inventive hydrogenation, 6-hydroperoxycaproic acid and/or 5-formylvaleric acid, dissolved in water or the organic solvents specified as extractants, are suitable.

The catalysts used for the catalytic hydrogenation in step c) of the process according to the invention are those which comprise at least one metal of groups 7 to 12 of the Periodic Table, for example ruthenium, nickel, cobalt, iron, rhenium, iridium, copper, osmium and zinc, excluding palladium, platinum and rhodium where they are the sole catalytic components.

Preference is given to the metals ruthenium, nickel, cobalt, rhenium and copper. These metals can be used either in the form of the metals or of their compounds, for example oxides and sulfides.

Preference is further given to mixtures or alloys of at least two of the metals of groups 7 to 12 of the Periodic Table. Examples include palladium/rhenium, platinum/rhenium and cobalt/copper.

Also very suitable are unsupported catalysts which do not comprise any support and consist of metals, metal oxides or mixtures thereof. Preference is given to unsupported iron and especially cobalt catalysts.

The metals or metal compounds can be used without support. However, preference is given to applying them to supports, for example $TiO_2$, $Al_2O_3$, $ZrO_2$, $SiO_2$, $HfO_2$, carbon, zeolites or mixtures thereof. These supported catalysts can be used in a wide variety of different finishing forms, for example extrudates, tablets or rings.

Copper, nickel and cobalt can preferably be used in the form of Raney nickel, Raney copper or Raney cobalt. The Raney catalysts can also be used in all known finishing forms, for example as tablets, extrudates or granules. Suitable Raney copper catalysts are, for example, Raney copper nuggets, which are described in WO-A 99/03.801.

Also particularly suitable for the hydrogenation in step c) of the process according to the invention is a catalyst comprising ruthenium supported on titanium dioxide shaped bodies, said titanium dioxide shaped bodies being obtained by treating titanium dioxide, before or after the shaping to the shaped body, with from 0.1 to 30% by weight of an acid in which titanium dioxide is sparingly soluble.

The catalytically active ruthenium is applied by processes known per se, preferably to prefabricated $TiO_2$ as a support material.

A titanium dioxide support suitable with preference for use in the ruthenium-comprising catalyst can be obtained according to DE-A 197 38 464 by treating titanium dioxide, before or after the shaping of the shaped body, with from 0.1 to 30% by weight of an acid, based on titanium dioxide, in which the titanium dioxide is sparingly soluble. Preference is given to using titanium dioxide in the anatase modification. Suitable acids of this type are, for example, formic acid, phosphoric acid, nitric acid, acetic acid or stearic acid.

The ruthenium active component can be applied in the form of a ruthenium salt solution to the titanium dioxide support thus obtained in one or more impregnation stages. Subsequently, the impregnated support is dried and if appropriate calcined. However, it is also possible to precipitate ruthenium from a ruthenium salt solution, preferably with sodium carbonate, onto a titanium dioxide present in powder form in aqueous suspension. The precipitated solids are washed, dried, if appropriate calcined and shaped. In addition, it is possible to convert volatile ruthenium compounds, for example ruthenium acetylacetonate or ruthenium carbonyl, to the gas phase and apply them to the support in a manner known per se, which is referred to as chemical vapor deposition.

The supported catalysts thus obtained may be present in all known finishing forms. Examples are extrudates, tablets or granules. Before use, the ruthenium catalyst precursors are reduced by treating with hydrogenous gas, preferably at temperatures above 100° C. Preference is given to passivating the catalysts, before use in the process according to the invention, at temperatures of from 0 to 50° C., preferably at room temperature, with oxygenous mixtures, preferably with air-nitrogen mixtures. However, it is also possible to install the catalyst into the hydrogenation reactor in oxidic form and to reduce it under reaction conditions.

The catalyst which is particularly preferred in accordance with the invention has a ruthenium content of from 0.1 to 10% by weight, preferably from 2 to 6, based on the total weight of the catalyst composed of catalytically active metal and support. The inventive catalyst may have a sulfur content of from 0.01 to 1% by weight, based on the total weight of the catalyst, the sulfur determination being effected coulometrically.

The ruthenium surface area is from 1 to 20 m$^2$/g, preferably from 5 to 15, and the BET surface area (determined to DIN 66131) is from 5 to 500 m$^2$/g, preferably from 50 to 200 m$^2$/g.

The inventive catalysts have a pore volume of from 0.1 to 1 ml/g. In addition, the catalysts are notable for a cutting hardness of from 1 to 100 N.

The hydrogenation catalysts may be suspended in the reaction mixture. Preference is given to arranging them in fixed bed form in the hydrogenation reactor. The hydrogenation can be performed batchwise or preferably continuously. The reaction mixture can be passed over the catalyst in liquid phase mode or trickle mode.

The starting mixture of the hydrogenation comprises two different compounds, 6-hydroperoxycaproic acid and 5-formylvaleric acid, since both are to be hydrogenated to 6-hydroxycaproic acid. Since a hydroperoxy group has to be hydrogenated in one case but an aldehyde group in another case, the optimal hydrogenation conditions of the two compounds differ.

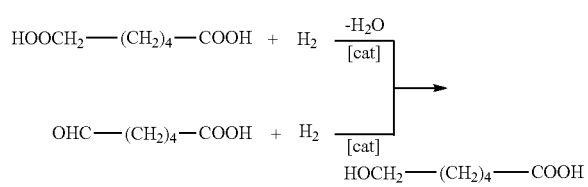

Since the hydroperoxycaproic acid can also be converted purely thermally, but less selectively than in a hydrogenation, to 6-hydroxycaproic acid, it can be hydrogenated according to DE-A 1 951 250 in the presence of palladium, rhodium or platinum catalysts at from 15 to 130° C., preferably from 50 to 100° C., i.e. at moderate temperatures.

The comparative example shows that aldehyde groups are hydrogenated only to a minor degree, if at all, under the conditions of the 6-hydroperoxycaproic acid hydrogenation in DE-A 1 951 250. For this purpose, higher temperatures and pressures are needed.

The hydrogenation in step c) of the process according to the invention can be carried out in a single reactor or in two reactors connected in series. When two reactors are used, the two reactors may comprise the same catalyst or two different catalysts. The two reactors may differ in the hydrogenation temperature and the partial hydrogen pressure.

It is also possible to carry out the hydrogenation in a single reactor filled with a single catalyst, such that the hydrogenation temperature within the reactor rises within a desired temperature range.

The hydrogenation in step c) of the process according to the invention is effected, irrespective of whether step a) has been conducted in the presence or absence of a catalyst, at temperatures of from more than 100 to 200° C., preferably from 120 to 180° C., more preferably from 130 to 170° C. The partial hydrogen pressure is from 1 to 100 bar, preferably from 2 to 80 bar, more preferably from 5 to 60 bar.

In step a) of the process according to the invention, a starting mixture which has been oxidized without catalyst is used. However, the use of catalysts is also possible in step a). When catalysts, for example cobalt carboxylates, are used, not only 6-hydroxycaproic acid but also only small amounts of 6-hydroperoxycaproic acid are formed. In this case, the hydrogenation of predominantly 5-formylvaleric acid is effected in step c) of the process according to the invention.

Useful alcohols for the carboxylic acids to be converted for the esterification in step d) of the process according to the invention—6-hydroxycaproic acid and α,ω-dicarboxylic acids having from four to six carbon atoms—are generally alkanols having from 1 to 12 carbon atoms, cycloalkanols having from 5 to 7 carbon atoms, aralkanols having from 7 to 8 carbon atoms or phenols having from 6 to 9 carbon atoms. It is possible to use methanol, ethanol, propanol, isopropanol, n- or i-butanol or else n-pentanol or i-pentanol, or mixtures of the alcohols, but preferably alcohols having from 1 to 4 carbon atoms, more preferably methanol. The ester groups in the 6-hydroxycaproic esters and the adipic esters may be the same or different, but they are preferably the same.

The product obtained from step c) of the process according to the invention is generally an aqueous solution having a water content of from 20 to 80%. Since an esterification reaction is an equilibrium reaction in which water forms, it is advisable, especially when esterifying with, for example, methanol, to remove water present before the reaction, in particular when it is impossible to remove water, for example azeotropically, during the esterification reaction. The dewatering can be effected, for example, with a membrane system, or preferably in a distillation apparatus, in which water is removed via the top and higher dicarboxylic acids via the bottom at from 10 to 250° C., preferably from 20 to 200° C., more preferably from 30 to 200° C., and a pressure of from 1 to 1500 mbar, preferably from 5 to 1100 mbar, more preferably from 20 to 1000 mbar. The bottom temperature is preferably selected such that the bottom product can be drawn off in liquid form. The water content in the bottom of the column may be from 0.01 to 10% by weight, preferably from 0.01 to 5% by weight, more preferably from 0.01 to 1% by weight.

An alcohol having from 1 to 10 carbon atoms is added to the dewatered hydrogenation output. It is possible to use either methanol, ethanol, propanol or isopropanol or mixtures of the alcohols, but preferably methanol, or C$_4$ and higher alcohols, especially having from 4 to 8 carbon atoms and preferably n- or i-butanol, or else n-pentanol or i-pentanol. The mixing ratio of alcohol to carboxylic acid stream (mass ratio) may be from 0.1 to 30, preferably from 0.2 to 20, more preferably from 0.5 to 10.

This mixture passes as a melt or solution into the reactor in which the carboxylic acids are esterified with the alcohol. The esterification reaction can be carried out at from 50 to 400° C., preferably from 70 to 300° C., more preferably from 90 to 200° C. It is possible to apply an external pressure, but preference is given to performing the esterification under autogenous pressure of the reaction system. The esterification apparatus used may be a stirred tank or flow tube, or it is possible to use a plurality of each. The residence time needed for the esterification is between 0.3 and 10 hours, preferably from 0.5 to 5 hours. The esterification reaction can proceed without addition of a catalyst, but preference is given to increasing the reaction rate by adding a catalyst. The catalyst may be a homogeneously dissolved catalyst or a solid catalyst. Examples of homogeneous catalysts include sulfuric acid, phosphoric acid, hydrochloric acid, sulfonic acids such as p-toluenesulfonic acid, heteropolyacids such as tungstophosphoric acid, or Lewis acids, for example aluminum, vanadium, titanium and boron compounds. Preference is given to mineral acids, especially sulfuric acid. The weight ratio of homogeneous catalyst to carboxylic acid melt is generally from 0.0001 to 0.5, preferably from 0.001 to 0.3.

Suitable solid catalysts are acidic or superacidic materials, for example acidic and superacidic metal oxides such as $SiO_2$, $Al_2O_3$, $SnO_2$, $ZrO_2$, sheet silicates or zeolites, all of which may be doped with mineral acid residues such as sulfate or phosphate to increase the acid strength, or organic ion exchangers with sulfonic acid or carboxylic acid groups. The solid catalysts may be arranged as a fixed bed or be used as a suspension.

The water formed in the reaction is appropriately removed continuously, for example through a membrane or by distillation.

When the hydrogenation in step c) of the process according to the invention has been performed in an organic solvent (extractant for 6-hydroxycaproic acid), for example methylcyclohexane, the esterification can be carried out in this solvent and the water of reaction can be removed after phase separation.

The completeness of the conversion of the free carboxyl groups present in the carboxylic acid melt is determined by the acid number (mg KOH/g) measured after the reaction. Minus any acid added as a catalyst, it is from 0.01 to 50 and preferably from 0.1 to 10 mg/KOH. Not all carboxyl groups present in the system need be present as esters of the alcohol used, but rather a portion may be present in the form of dimeric or oligomeric esters with the OH end of the hydroxycaproic acid.

The esterification mixture from step d) of the process according to the invention is fed into a membrane system or preferably a distillation column. When a dissolved acid has been used as the catalyst for the esterification reaction, the esterification mixture is appropriately neutralized with a base, in which case from 1 to 1.5 base equivalents are added per acid equivalent of the catalyst. The bases used are generally alkali metal or alkaline earth metal oxides, carbonates, hydroxides or alkoxides, or amines in substance or dissolved in the esterification alcohol. However, it is also possible to neutralize with basic ion exchangers.

When a column is used, the feed to the column is preferably between the top stream and the bottom stream. The excess esterification alcohol, water and low boilers are drawn off via the top at pressures of from 1 to 1500 mbar, preferably from 20 to 1000 mbar, more preferably from 40 to 800 mbar, and temperatures between 0 and 150° C., preferably 15 and 90° C. and especially 25 and 75° C. Low boilers are components which have a lower boiling point than 6-hydroxycaproic esters and adipic esters.

The bottoms obtained are an ester mixture which comprises predominantly the esters of the alcohol used with dicarboxylic acids such as adipic acid and glutaric acid, hydroxycarboxylic acids such as 6-hydroxycaproic acid, and oligomers and free and esterified 1,2- and 1,4-cyclohexanediols. It may be advisable to permit a residual content of water and/or alcohol up to 4% by weight each in the ester mixture. The bottom temperatures are from 70 to 250° C., preferably from 80 to 220° C., more preferably from 100 to 190° C.

The stream which has been substantially freed of water and esterification alcohol is fed into a further distillation column. The column is operated at temperatures of from 10 to 300° C., preferably from 20 to 270° C., more preferably from 30 to 250° C., and pressures of from 1 to 1000 mbar, preferably from 5 to 500 mbar, more preferably from 10 to 200 mbar.

The top fraction consists predominantly of residual water and residual alcohol, esters of the alcohol with monocarboxylic acids, predominantly $C_3$-$C_6$-monocarboxylic esters with hydroxycarboxylic acids, such as 6-hydroxycaproic acid, 5-hydroxyvaleric acid, and in particular the diesters with dicarboxylic acids such as adipic acid, glutaric acid and succinic acid, and also cyclohexanediols, caprolactone and valerolactone.

The components mentioned can be removed together via the top or, in a further preferred embodiment, separated in a column of stage 4 into a top stream which comprises predominantly residual water and residual alcohol and the abovementioned constituents having from 3 to 5 carbon atoms, and a side stream which comprises predominantly the abovementioned constituents of the $C_6$ esters.

The high-boiling components having a boiling point above those of 6-hydroxycaproic esters and adipic esters, predominantly comprising dimeric or oligomeric esters, cyclohexanediols and constituents not defined in detail, some of them polymeric, are removed via the stripping section of the column.

For the caprolactone preparation, the stream comprising predominantly esters of the $C_6$ acids from step d) of the process according to the invention is used. To this end, this stream is separated in a distillation column into a stream comprising predominantly adipic esters via the top, and a stream comprising predominantly 6-hydroxycaproic esters via the bottom. The column is operated at pressures of from 1 to 500 mbar, preferably from 5 to 350 mbar, more preferably from 10 to 200 mbar, and bottom temperatures of from 80 to 250° C., preferably from 100 to 200° C., more preferably from 110 to 180° C. The top temperatures are established correspondingly.

An important factor for a high purity and high yield of caprolactone is the removal of the 1,2-cyclohexanediols from the 6-hydroxycaproic ester, since these components can form azeotropes with one another.

The 6-hydroxycaproic ester stream which comprises from 0 to 40% by weight of adipic esters can be converted to alcohol and caprolactone in the gas phase or liquid phase.

The process according to the invention for preparing 6-hydroxycaproic esters possesses a series of advantages over the prior art:

The hydrogenation of 5-formylvaleric acid enhances the 6-hydroxycaproic acid yield, since otherwise the corresponding esters are obtained only from the 6-hydroxycaproic acid. A further advantage is that it is no longer necessary to remove the 6-hydroxycaproic esters from 5-formylvaleric esters in the process according to the invention.

Moreover, the process according to the invention can be simplified with respect to the prior art by allowing a portion of the adipic acid to crystallize out of the aqueous solution after water has been evaporated off. A further advantageous possibility consists in removing 6-hydroperoxy- and 6-hydroxycaproic acid from adipic acid by extraction with organic solvents. This deburdens the distillative 6-hydroxycaproic ester/adipic ester separation.

EXAMPLES

The Analyses were Carried Out by Means of Gas Chromatography

Example 1

Analogously to the process described in DE-A 1 951 250 example 1, 100 g of the product obtained according to 1b of the patent, which, according to gas chromatography analysis, still comprised 4.5% 5-formylvaleric acid, were dissolved in water (in a proportion of 50% by weight) and hydrogenated at 130° C. and hydrogen pressure 35 bar in a stirred autoclave over a catalyst which had been activated at 250° C. with hydrogen beforehand (catalyst composition in oxidic form: 23% NiO, 8% CuO, 2% $Mn_2O_3$ on $SiO_2$). After a reaction time of 10 h, the content (calculated without water) of 5-formylvaleric acid had fallen to 0.1%, and the content of 6-hydroxycaproic acid had risen correspondingly from approx. 4% to approx. 64%.

All other components remained virtually unchanged. This hydrogenation output mixture was freed of water by distillation, admixed with 0.2% sulfuric acid and 200 g of methanol, and heated to 130° C. under autogenous pressure for 5 h. After cooling, the sulfuric acid was neutralized with equimolar amounts of sodium carbonate and the mixture was fractionally distilled. At standard pressure, first methanol, then water, were removed, then several fractions which comprised methyl 6-hydroxycaproate with a purity of up to 99.2% were obtained at 10 mbar.

Example 2

Example 1 is repeated, with the difference that the aqueous extract according to DE-A 1 951 250 example 1a) (prepared as described in French patent 1 491 518) was used in the hydrogenation. The hydrogenation output included 0.2% 5-formylvaleric acid but no 6-hydroperoxycaproic acid. The content of 6-hydroxycaproic acid was approx. 64% as in example 1. For further results see table 1.

Example 3

Example 2 was repeated. The hydrogenation catalyst used was a catalyst which, in the oxidic state, has the following composition: 66% CoO, 20% CuO, 7% $Mn_2O_3$, further components: alkali metal and alkaline earth metal oxides and phosphorus oxides. The hydrogenation was effected at 150° C. For results see table 1.

Example 4

Example 2 was repeated. The hydrogenation catalyst used was Ru (5% calculated as the oxide) on activated carbon. The hydrogenation was effected at 130° C. For results see table 1.

Example 5

Example 2 was repeated. The hydrogenation catalyst used was Re (6% calculated as the oxide) on activated carbon. The hydrogenation was performed at 155° C. For results see table 1.

TABLE 1

| Example | Residual 5-formylvaleric acid content after hydrogenation (%) | Purity of methyl 6-hydroxycaproate (%) |
|---|---|---|
| 2 | 0.1 | 99.1 |
| 3 | 0.02 | 99.4 |
| 4 | <0.02 | 99.5 |
| 5 | 0.08 | 99.0 |

Comparative Example 1

Example 2 was repeated, except hydrogenating over a Pd (5% as PdO) on carbon catalyst. The content of hydroperoxide was zero thereafter, but the content of 5-formylvaleric acid had fallen only to 3.9%. After esterification and distillation, methyl 6-hydroxycaproate with a maximum purity of 98.1% was obtained.

Comparative Example 2

Example 1 from DE-A 1 951 250 was repeated. The starting content of 5-formylvaleric acid of 4.5% before the hydrogenation was unchanged after the hydrogenation.

The invention claimed is:

1. A process, comprising:
   a) oxidizing cyclohexane with molecular oxygen or mixtures of molecular oxygen and gases which are inert under the reaction conditions to give a reaction mixture which comprises cyclohexyl hydroperoxide, cyclohexanol, cyclohexanone, cyclohexane, 6-hydroxycaproic acid, 6-hydroxycaproic acid, 5-formylvaleric acid, and at least one α,ω-dicarboxylic acid having from four to six carbon atoms;
   b) separating the reaction mixture from a), after adding water, into an organic phase comprising cyclohexane and the cyclohexane compounds, and an aqueous phase comprising the carboxylic acids;
   c) catalytically hydrogenating the aqueous phase from b);
   d) reacting the carboxylic acids present in the aqueous phase with an alcohol comprising from 1 to 10 carbon atoms to give the corresponding carboxylic esters, to yield an esterification mixture; and
   e) distilling out a 6-hydroxycaproic ester from the esterification mixture from d), to obtain at least one 6-hydroxycaproic ester,
   wherein the catalytically hydrogenating in c) comprises hydrogenating 5-formylvaleric acid to 6-hydroxycaproic acid in the presence of a catalyst, which comprises at least one metal selected from the group consisting of ruthenium, nickel, cobalt, rhenium, and copper, and
   wherein the hydrogenating in c) is performed at a temperature of from 100 to 200° C. and a pressure of from 1 to 100 bar.

2. The process according to claim 1, wherein said a) oxidizing is performed in the presence of a catalyst.

3. The process according to claim 1, wherein said a) oxidizing is performed in the absence of a catalyst.

4. The process according to claim 1, wherein the catalytically hydrogenating in c) further comprises catalytically hydrogenating 6-hydroxycaproic acid to 6-hydroxycaproic acid.

5. The process according to claim 1, further comprising adding an aliphatic, a cycloaliphatic or an aromatic hydrocarbon to the aqueous phase in b), which comprises the carboxylic acids, to remove cyclohexyl hydroperoxide, cyclohexanol, and cyclohexanone present in the aqueous phase.

6. The process according to claim 1, further comprising adding an organic, inert solvent to the aqueous phase to extract 6-hydroxycaproic acid and 6-hydroxycaproic acid from the aqueous phase.

7. The process according to claim 1, further comprising distilling the aqueous phase comprising the carboxylic acids to remove water from the aqueous phase, and
   precipitating carboxylic acids from the aqueous phase.

8. The process according to claim 1, wherein the hydrogenating in c) is performed at a temperature of from 130 to 170° C. and a pressure of from 5 to 60 bar.

9. The process according to claim 2, wherein the catalytically hydrogenating in c) further comprises catalytically hydrogenating 6-hydroxycaproic acid to 6-hydroxycaproic acid.

10. The process according to claim 3, wherein the catalytically hydrogenating in c) further comprises catalytically hydrogenating 6-hydroperoxycaproic acid to 6-hydroxycaproic acid.

11. The process according to claim 2, further comprising adding an aliphatic, a cycloaliphatic or an aromatic hydrocarbon to the aqueous phase in b), which comprises the carboxylic acids, to remove cyclohexyl hydroperoxide, cyclohexanol, and cyclohexanone present in the aqueous phase.

12. The process according to claim 3, further comprising adding an aliphatic, a cycloaliphatic or an aromatic hydrocarbon to the aqueous phase in b), which comprises the carboxylic acids, to remove cyclohexyl hydroperoxide, cyclohexanol, and cyclohexanone present in the aqueous phase.

13. The process according to claim 4, further comprising adding an aliphatic, a cycloaliphatic or an aromatic hydrocarbon to the aqueous phase in b), which comprises the carboxylic acids, to remove cyclohexyl hydroperoxide, cyclohexanol, and cyclohexanone present in the aqueous phase.

14. The process according to claim 2, further comprising adding an organic, inert solvent to the aqueous phase to extract 6-hydroxycaproic acid and 6-hydroxycaproic acid from the aqueous phase.

15. The process according to claim 3, further comprising adding an organic, inert solvent to the aqueous phase to extract 6-hydroxycaproic acid and 6-hydroxycaproic acid from the aqueous phase.

16. The process according to claim 4, further comprising adding an organic, inert solvent to the aqueous phase to extract 6-hydroxycaproic acid and 6-hydroxycaproic acid from the aqueous phase.

17. The process according to claim 5, further comprising adding an organic, inert solvent to the aqueous phase to extract 6-hydroxycaproic acid and 6-hydroxycaproic acid from the aqueous phase.

18. The process according to claim 2, further comprising distilling the aqueous phase comprising the carboxylic acids to remove water from the aqueous phase, and
precipitating carboxylic acids from the aqueous phase.

19. The process according to claim 3, further comprising distilling the aqueous phase comprising the carboxylic acids to remove water from the aqueous phase, and
precipitating carboxylic acids from the aqueous phase.

20. The process according to claim 4, further comprising distilling the aqueous phase comprising the carboxylic acids to remove water from the aqueous phase, and
precipitating carboxylic acids from the aqueous phase.

21. The process according to claim 1, wherein the catalyst comprises at least one metal selected from the group consisting of ruthenium, nickel, rhenium, and copper.

22. The process according to claim 1, wherein the catalyst comprises at least one metal selected from the group consisting of ruthenium, nickel, and copper.

23. The process according to claim 1, wherein the catalyst comprises at least one member selected from the group consisting of ruthenium, rhenium, a mixture of nickel and copper, and a mixture of cobalt and copper.

24. The process according to claim 1, wherein the catalyst comprises at least one metal selected from the group consisting of ruthenium and rhenium.

25. The process according to claim 1, wherein said aqueous phase comprises at most 0.1% by weight of 5-formylvaleric acid after said c) catalytically hydrogenating is carried out.

26. The process according to claim 1, wherein said catalyst excludes palladium, platinum and rhodium as individual catalysts.

* * * * *